(12) United States Patent
Liang et al.

(10) Patent No.: US 8,865,905 B2
(45) Date of Patent: Oct. 21, 2014

(54) ORGANIC COMPOUNDS

(71) Applicant: General Electric Company, Schenectady, NY (US)

(72) Inventors: Yangang Liang, Shanghai (CN); Shengxia Liu, Shanghai (CN); Rui Wang, Chengdu (CN); Jie Liu, Niskayuna, NY (US); Kelly Scott Chichak, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 13/848,178

(22) Filed: Mar. 21, 2013

(65) Prior Publication Data

US 2013/0217882 A1 Aug. 22, 2013

Related U.S. Application Data

(62) Division of application No. 13/424,531, filed on Mar. 20, 2012, now Pat. No. 8,426,601, and a division of application No. 12/492,716, filed on Jun. 26, 2009, now Pat. No. 8,178,682.

(51) Int. Cl.
*C07D 213/127* (2006.01)
*C07D 213/30* (2006.01)
*H01L 51/00* (2006.01)
*C07D 213/26* (2006.01)

(52) U.S. Cl.
CPC .......... *H01L 51/0067* (2013.01); *C07D 213/30* (2013.01); *C07D 213/127* (2013.01); *C07D 213/26* (2013.01)
USPC ........................................................ 546/255

(58) Field of Classification Search
CPC .................................................. C07D 213/127
USPC ........................................................ 546/255
See application file for complete search history.

(56) References Cited

U.S. PATENT DOCUMENTS

| 7,011,897 | B2 | 3/2006 | Thompson et al. |
| 7,410,702 | B2 | 8/2008 | Jaycox et al. |
| 7,709,100 | B2 | 5/2010 | Kwong et al. |
| 7,777,043 | B2 | 8/2010 | Yabe et al. |
| 8,039,125 | B2 * | 10/2011 | Ye et al. ............... 428/690 |
| 2004/0075096 | A1 | 4/2004 | Grushin et al. |
| 2005/0238918 | A1 | 10/2005 | Igarashi |
| 2007/0132370 | A1 | 6/2007 | Boerner et al. |
| 2008/0111480 | A1 | 5/2008 | Lee et al. |

FOREIGN PATENT DOCUMENTS

| CN | 1681904 A | 10/2005 |
| CN | 1833470 A | 9/2006 |
| CN | 101076902 A | 11/2007 |
| JP | 2005082730 | 3/2005 |
| JP | 2008120696 | 5/2008 |
| JP | 2008127316 | 6/2008 |
| JP | 2008127326 | 6/2008 |
| JP | 2009141339 | 6/2009 |
| WO | WO2009142867 A1 | 11/2009 |
| WO | WO2009142870 A1 | 11/2009 |
| WO | WO2010072300 A1 | 7/2010 |
| WO | WO2010080471 A1 | 7/2010 |
| WO | WO2010080472 A1 | 7/2010 |

OTHER PUBLICATIONS

Mikroyannidis, "Synthesis by Heck Coupling of Soluble, Blue-Light-Emitting Fully Conjugated Poly(p-phenylenevinylene)s With Highly Phenylated Side Groups", Macromolecules, vol. 35, No. 25, pp. 9289-9295, 2002.
Suzuki, "Carbon-Carbon Bonding Made Easy", Chem. Commun., pp. 4759-4763, 2005.
Su, Shi-Jian, et al., "Pyridine-Containing Bipolar Host Materials for Highly Efficient Blue Phosphorescent OLEDs", Chem. Mater., Feb. 12, 2008, pp. 1691-1693, vol. No. 20, Issue No. 5.
Su, Shi-Jian, et al., "Novel Four-Pyridylbenzene-Armed Biphenyls as Electron-Transport Materials for Phosphorescent OLEDs", Organic Letters, Feb. 1, 2008, pp. 941-944, vol. No. 10, Issue No. 5.
La-Ga, Tong, et al., "Optical and Electrical Properties of New-Type Blue Electroluminescence Materials of Phenylene-Pyridine Copolymers", Journal of Functional Materials, Feb. 25, 2003, pp. 80-82, vol. No. 34, Issue No. 01.
Unofficial English translation of CN Office Action issued Apr. 17, 2014 in connection with corresponding CN Patent Application No. 201080038664.7.

* cited by examiner

*Primary Examiner* — Patricia L Morris
(74) *Attorney, Agent, or Firm* — Mary Louise Stanford

(57) ABSTRACT

A compound of formula IV:

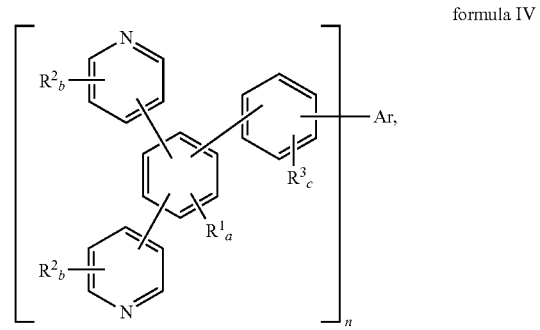

formula IV wherein $R^1$, $R^2$, and $R^3$ are, independently at each occurrence, a $C_1$-$C_{20}$ aliphatic radical, a $C_3$-$C_{20}$ aromatic radical, or a $C_3$-$C_{20}$ cycloaliphatic radical; Ar is heteroaryl, aryl, alkyl or cycloalkyl; b and c are, independently at each occurrence, an integer ranging from 0-4; a is an integer ranging from 0-3; and n is an integer ranging from 2 to 4.

11 Claims, No Drawings

ORGANIC COMPOUNDS

CROSS-REFERENCE TO RELATED APPLICATIONS

This application is a division of U.S. patent application Ser. No. 13/424,531, filed on Mar. 20, 2012, which is a division of U.S. patent application Ser. No. 12/492,716, filed on Jun. 26, 2009 which is now U.S. Pat. No. 8,178,682. The entire disclosures of U.S. patent application Ser. No. 13/424,531 and U.S. Pat. No. 8,178,682 are incorporated herein by reference.

BACKGROUND

The invention relates generally to processes for making organic compounds useful, e.g., as electron-transporting materials and/or hole blocking materials of optoelectronic devices and intermediates thereof, and the organic compounds made therefrom.

Optoelectronic devices, e.g. Organic Light Emitting Devices (OLEDs), which make use of thin film materials that emit light when subjected to a voltage bias, are expected to become an increasingly popular form of flat panel display technology. This is because OLEDs have a wide variety of potential applications, including cell phones, personal digital assistants (PDAs), computer displays, informational displays in vehicles, television monitors, as well as light sources for general illumination. Due to their bright colors, wide viewing angle, compatibility with full motion video, broad temperature ranges, thin and conformable form factor, low power requirements and the potential for low cost manufacturing processes, OLEDs are seen as a future replacement technology for cathode ray tubes (CRTs) and liquid crystal displays (LCDs). Due to their high luminous efficiencies, OLEDs are seen as having the potential to replace incandescent, and perhaps even fluorescent, lamps for certain types of applications.

OLEDs possess a sandwiched structure, which consists of one or more organic layers between two opposite electrodes. For instance, multi-layered devices usually comprise at least three layers: a hole injection/transport layer, an emissive layer and an electron transport layer (ETL). Furthermore, it is also preferred that the hole injection/transport layer serves as an electron blocking layer and the ETL as a hole blocking layer. Single-layered OLEDs comprise only one layer of materials between two opposite electrodes.

BRIEF DESCRIPTION

In one aspect, the invention relates to a process comprising:
reacting a compound of formula A and a compound of formula B to form a compound of formula C; and

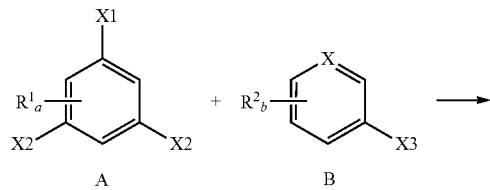

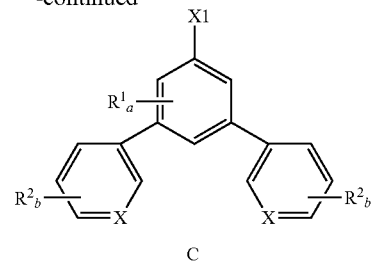

reacting one of the compound of formula C and the compound of formula D with a first boron esterification reagent to generate a boronic acid or a boronic ester to react with another of the compound of formula C and the compound of formula D to form a compound of formula E;

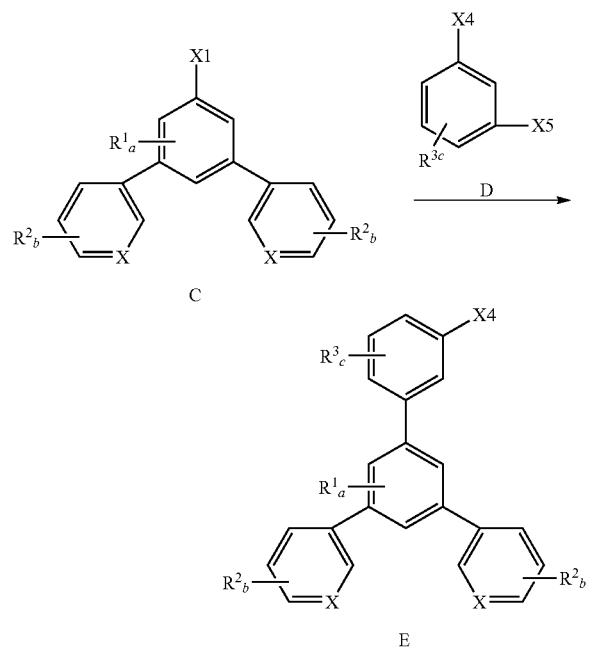

wherein $R^1$, $R^2$, and $R^3$ are, independently at each occurrence, a $C_1$-$C_{20}$ aliphatic radical, a $C_3$-$C_{20}$ aromatic radical, or a $C_3$-$C_{20}$ cycloaliphatic radical;

X1 is chloro, bromo, trifluoromethanesulfonate, or hydroxy;

X2 is chloro, bromo, iodo; and when X1 is chloro, X2 is bromo or iodo, when X1 is bromo, X2 is iodo, when X1 is hydroxy, X2 is chloro, bromo or iodo, when X1 is trifluoromethanesulfonate, X2 is bromo or iodo;

X3 is a boronic acid or boronic ester;

X is CH or N and when X is CH, at least one of $R^2$ is pyridyl;

X4 is chloro, bromo, trifluoromethanesulfonate, or hydroxy;

X5 is chloro, bromo, iodo; and when X4 is chloro, X5 is bromo or iodo, when X4 is bromo, X5 is iodo, when X4 is hydroxy, X5 is chloro, bromo or iodo, when X4 is trifluoromethanesulfonate, X5 is bromo or iodo;

a, and c are, independently at each occurrence, an integer ranging from 0-4; and b is an integer ranging from 0-3.

In another aspect, the invention relates to a compound of formula IV:

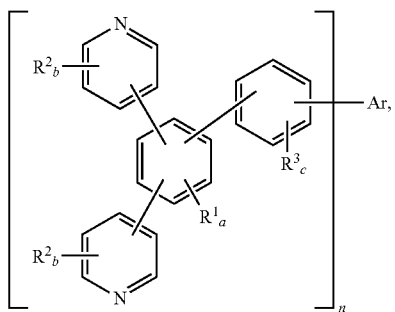

formula IV wherein
$R^1$, $R^2$, and $R^3$ are, independently at each occurrence, a $C_1$-$C_{20}$ aliphatic radical, a $C_3$-$C_{20}$ aromatic radical, or a $C_3$-$C_{20}$ cycloaliphatic radical;
Ar is heteroaryl, aryl, alkyl or cycloalkyl;
b and c are, independently at each occurrence, an integer ranging from 0-4;
a is an integer ranging from 0-3; and
n is an integer ranging from 2 to 4.

In yet another aspect, the invention relates to a process, comprising:

reacting a compound of formula F with 1-chloro-3,5-dibromobenzene to form a compound of formula G;

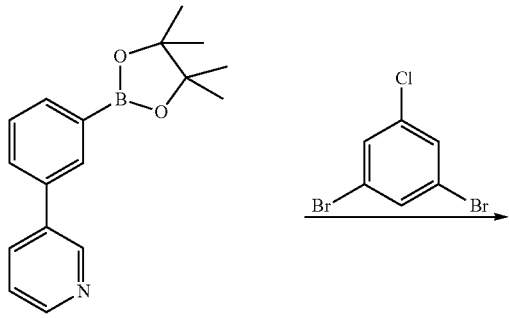

reacting the compound of formula G with pinacol diborane to form a compound of formula H;

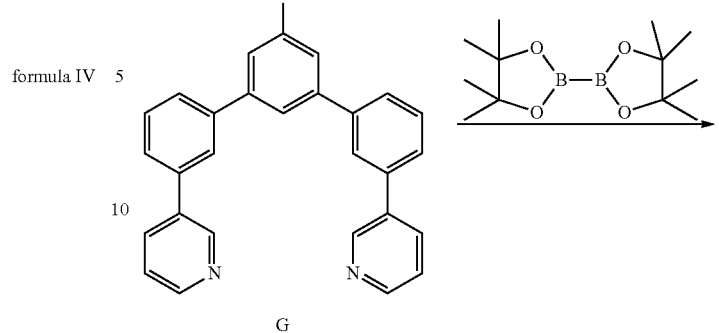

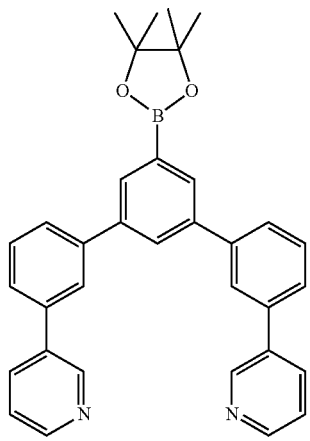

reacting the compound of formula H with 1-bromo-3-iodobenzene to form a compound of formula J; and

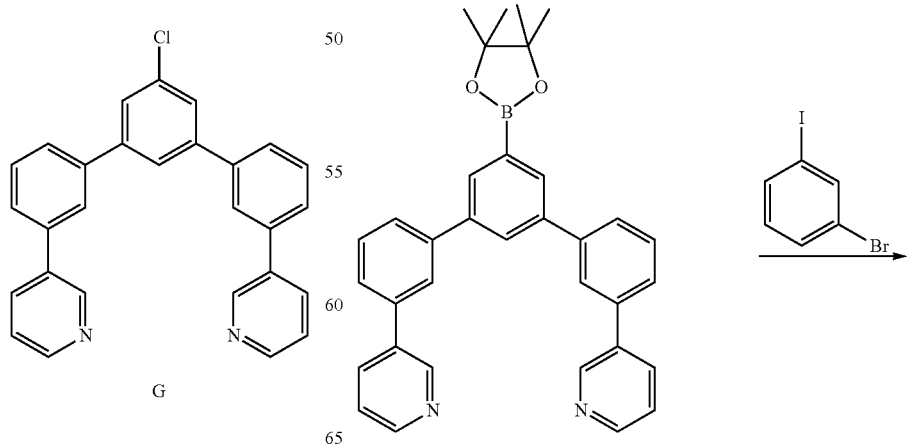

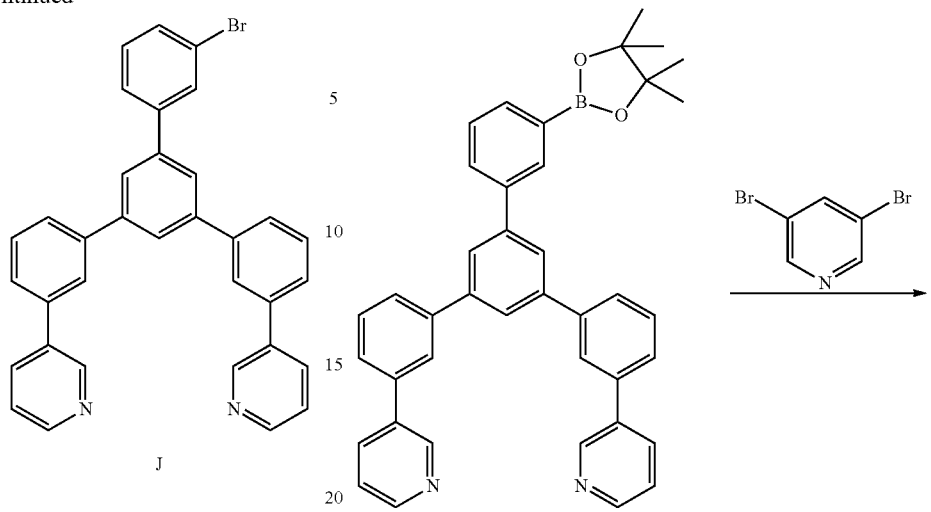
reacting the compound of formula J with pinacol diborane to form a compound of formula K; and
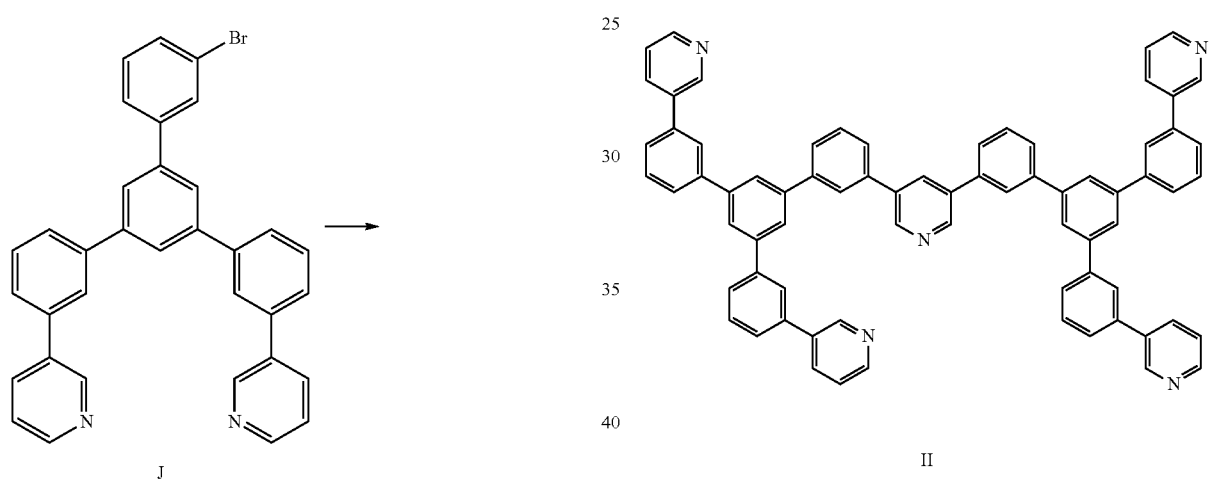
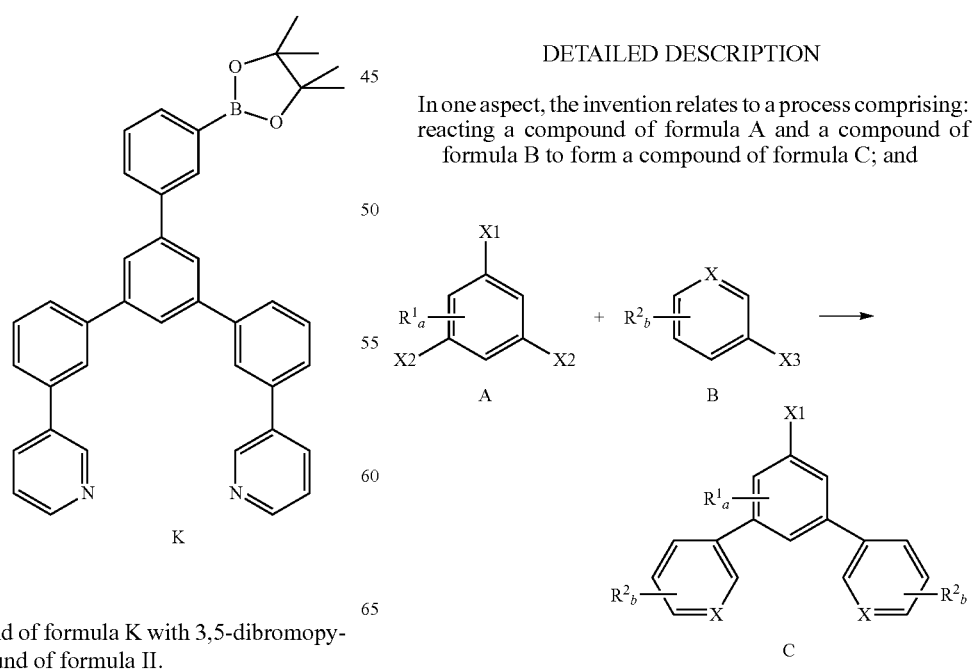
reacting the compound of formula K with 3,5-dibromopyridine to form a compound of formula II.
DETAILED DESCRIPTION
In one aspect, the invention relates to a process comprising: reacting a compound of formula A and a compound of formula B to form a compound of formula C; and reacting one of the compound of formula C and the compound of formula D with a first boron esterification reagent to generate a boronic acid or a boronic ester to react with another of the compound of formula C and the compound of formula D to form a compound of formula E;

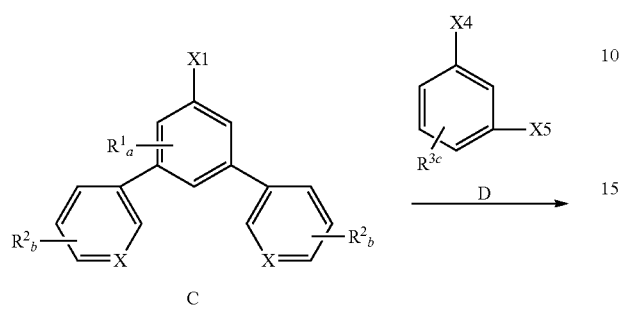

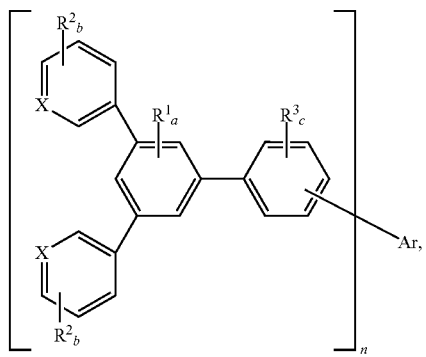

wherein Ar is heteroaryl, aryl, alkyl or cycloalkyl, n is an integer ranging from 2-4.

In some embodiments, the process further comprises converting the compound of formula E into a compound of formula:

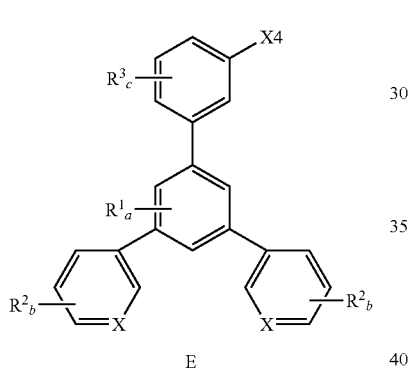

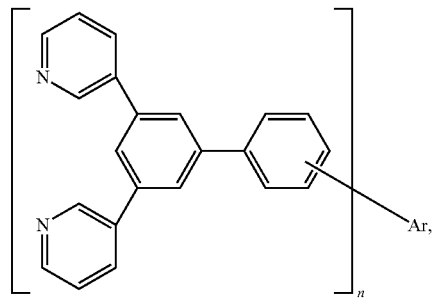

wherein $R^1$, $R^2$, and $R^3$ are, independently at each occurrence, a $C_1$-$C_{20}$ aliphatic radical, a $C_3$-$C_{20}$ aromatic radical, or a $C_3$-$C_{20}$ cycloaliphatic radical;

X1 is chloro, bromo, trifluoromethanesulfonate, or hydroxy;

X2 is chloro, bromo, iodo; and when X1 is chloro, X2 is bromo or iodo, when X1 is bromo, X2 is iodo, when X1 is hydroxy, X2 is chloro, bromo or iodo, when X1 is trifluoromethanesulfonate, X2 is bromo or iodo;

X3 is a boronic acid or boronic ester;

X is CH or N and when X is CH, at least one of $R^2$ is pyridyl;

X4 is chloro, bromo, trifluoromethanesulfonate, or hydroxy;

X5 is chloro, bromo, iodo; and when X4 is chloro, X5 is bromo or iodo, when X4 is bromo, X5 is iodo, when X4 is hydroxy, X5 is chloro, bromo or iodo, when X4 is trifluoromethanesulfonate, X5 is bromo or iodo;

a, and c are, independently at each occurrence, an integer ranging from 0-4; and b is an integer ranging from 0-3.

In some embodiments, the process further comprises converting the compound of formula E into a compound of formula:

wherein Ar is heteroaryl, aryl, alkyl or cycloalkyl, n is an integer ranging from 2-4.

In some embodiments, the process further comprises converting the compound of formula E into a compound of formula:

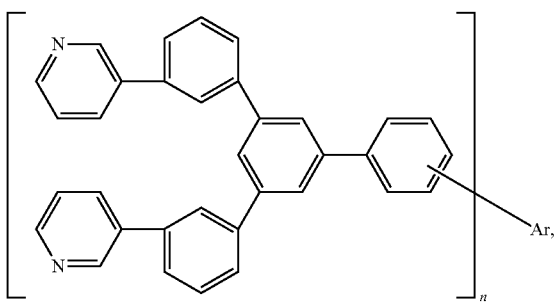

wherein Ar is heteroaryl, aryl, alkyl or cycloalkyl, n is an integer ranging from 2-4.

In some embodiments, the process further comprises reacting the compound of formula E with a second boron esterification reagent to generate a boronic acid or a boronic ester to react with a pyridyl dihalide to form a compound of formula I formula I

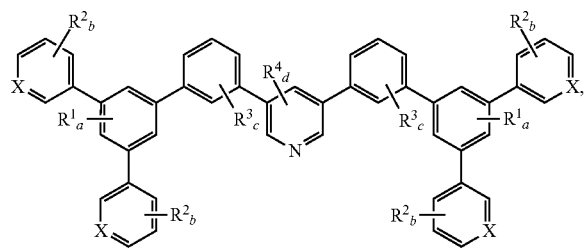

wherein

R¹, R², R³, and R⁴ are, independently at each occurrence, a C₁-C₂₀ aliphatic radical, a C₃-C₂₀ aromatic radical, or a C₃-C₂₀ cycloaliphatic radical;

X is CH or N and when X is CH, at least one of $R^2$ is pyridyl;

a, c, and d are, independently at each occurrence, an integer ranging from 0-4; and b is an integer ranging from 0-3.

In some embodiments, the first and the second boron esterification reagents are pinacol diborane and the pyridyl dihalide is

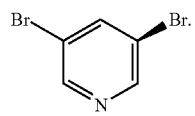

In some embodiments, the compound of formula D is of formula

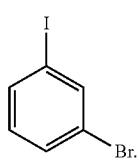

In some embodiments, the compound of formula A is 1-chloro-3,5-dibromobenzene and the compound of B is of formula

F

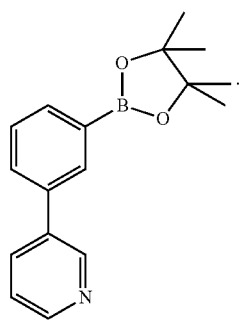

In some embodiments, the compound of formula C is of formula

G

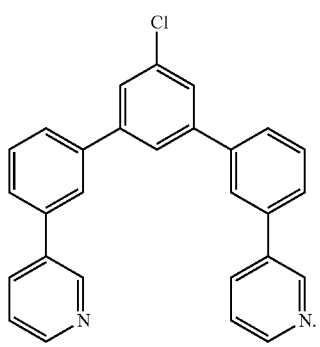

In some embodiments, the compound of formula C reacts with pinacol diborane to generate a compound of formula H to react with the compound of formula D.

formula H

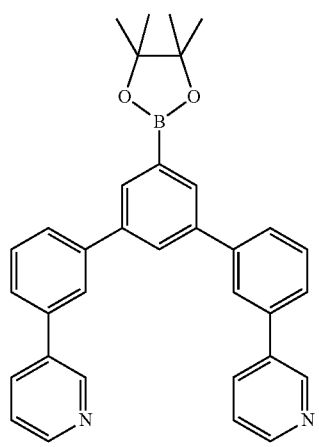

In some embodiments, the process further comprises reacting 3-(3-bromophenyl)pyridine with pinacol diborane to form the compound of formula F.

In some embodiments, the compound of formula E is of formula J

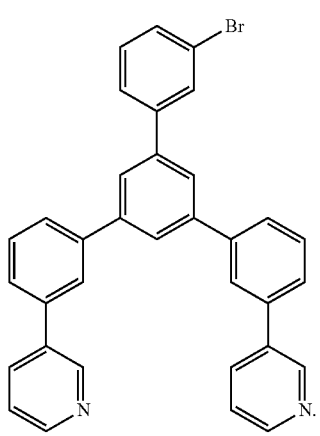

In some embodiments, the process further comprises converting the compound of formula J into a compound of formula K formula K

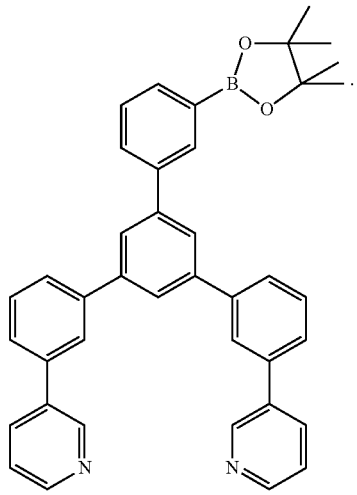

In some embodiments, the compound of formula I is of formula II formula II

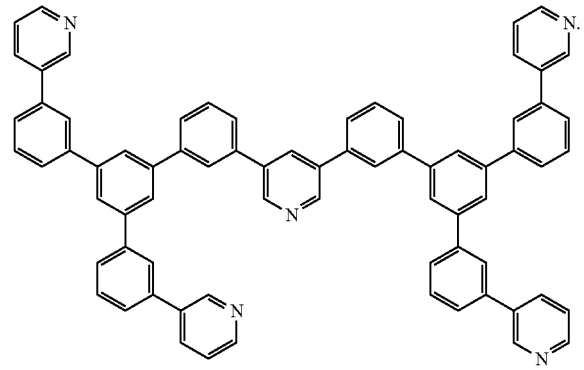

In some embodiments, the compound of formula C is of formula

L

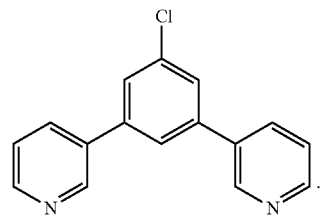

In some embodiments, the compound of formula A is 1-chloro-3,5-dibromobenzene and the compound of formula B is 3-pyridine boronic acid.

In some embodiments, the compound of formula C reacts with pinacol diborane to generate a compound of formula M to react with the compound of formula D.

formula M

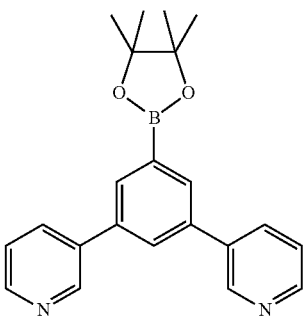

In some embodiments, the compound of formula E is of formula N

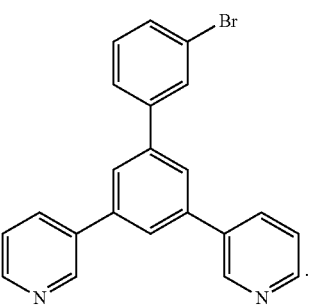

In some embodiments, the compound of formula I is of formula III formula III

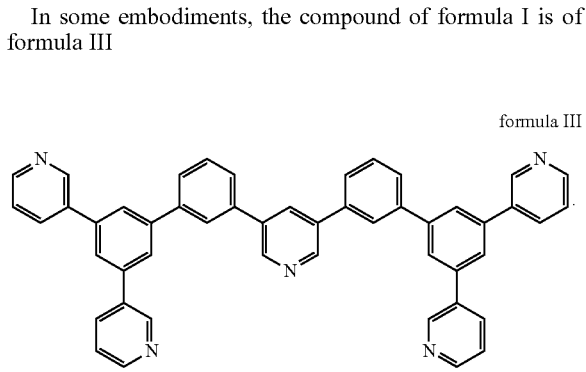

In some embodiments, the compound of formula A is selected from

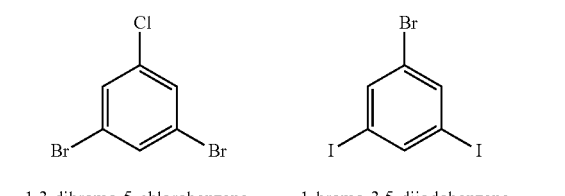

1,3-dibromo-5-chlorobenzene, 1-bromo-3,5-diiodobenzene or

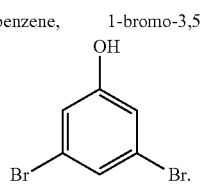

3,5-dibromophenol

In another aspect, the present invention relates to a compound of formula IV:

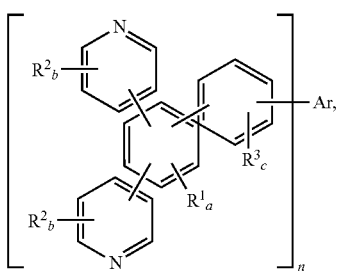

formula IV wherein
- $R^1$, $R^2$, and $R^3$ are, independently at each occurrence, a $C_1$-$C_{20}$ aliphatic radical, a $C_3$-$C_{20}$ aromatic radical, or a $C_3$-$C_{20}$ cycloaliphatic radical;
- Ar is heteroaryl, aryl, alkyl or cycloalkyl;
- b and c are, independently at each occurrence, an integer ranging from 0-4;
- a is an integer ranging from 0-3; and
- n is an integer ranging from 2 to 4.

In some embodiments, Ar is

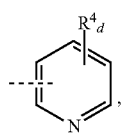

and $R^4$ is a $C_1$-$C_{20}$ aliphatic radical, a $C_3$-$C_2$ aromatic radical, or a $C_3$-$C_{20}$ cycloaliphatic radical and d is an integer ranging from 0-4.

In some embodiments, the compound is of formula III

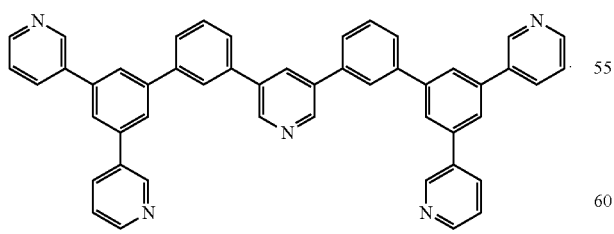

formula III

In another aspect, the present invention relates to a process, comprising:

reacting a compound of formula F with 1-chloro-3,5-dibromobenzene to form a compound of formula G;

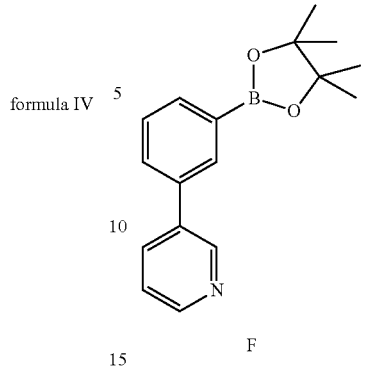

F

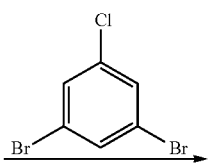

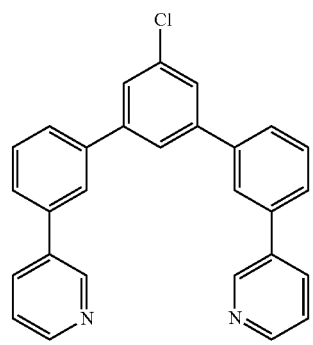

G reacting the compound of formula G with pinacol diborane to form a compound of formula H;

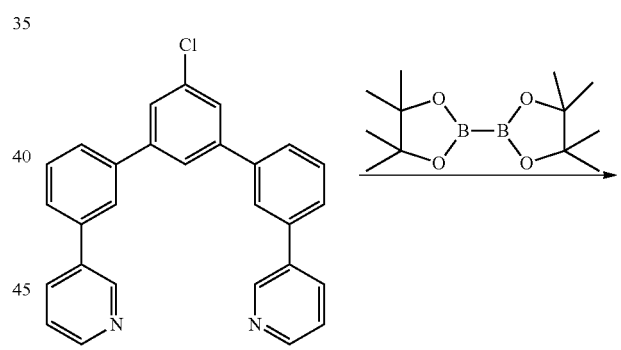

G

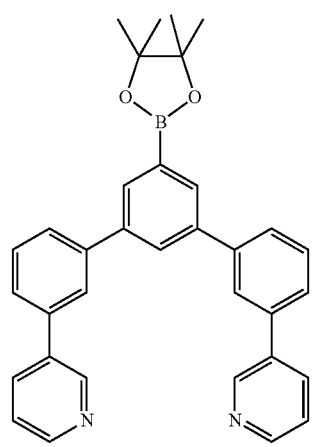

H reacting the compound of formula H with 1-bromo-3-iodobenzene to form a compound of formula J; and

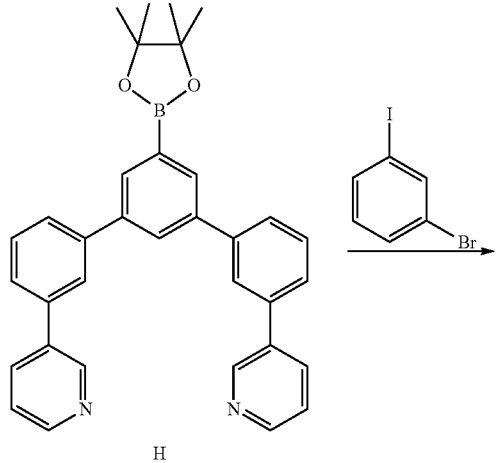

H

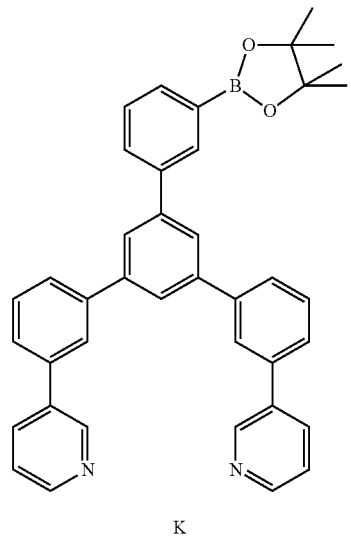

K reacting the compound of formula K with 3,5-dibromopyridine to form a compound of formula II.

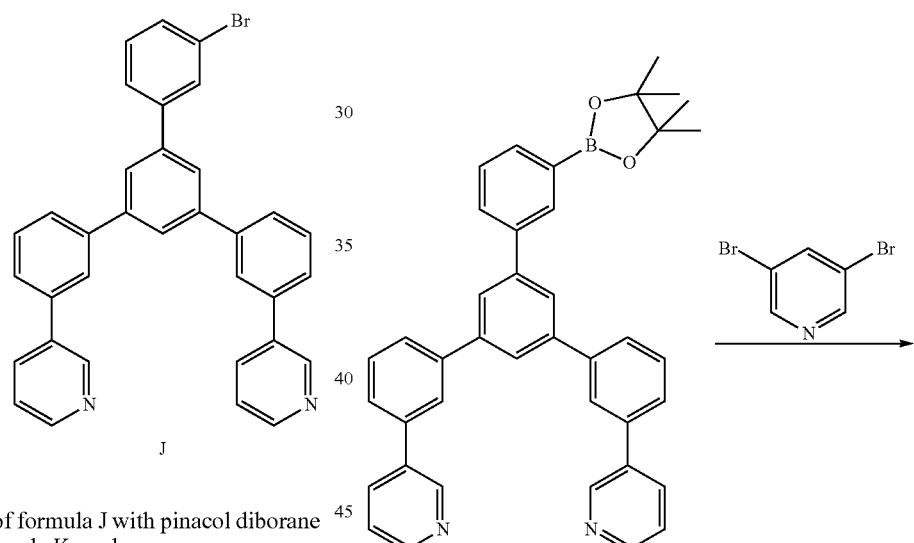

J reacting the compound of formula J with pinacol diborane to form a compound of formula K; and

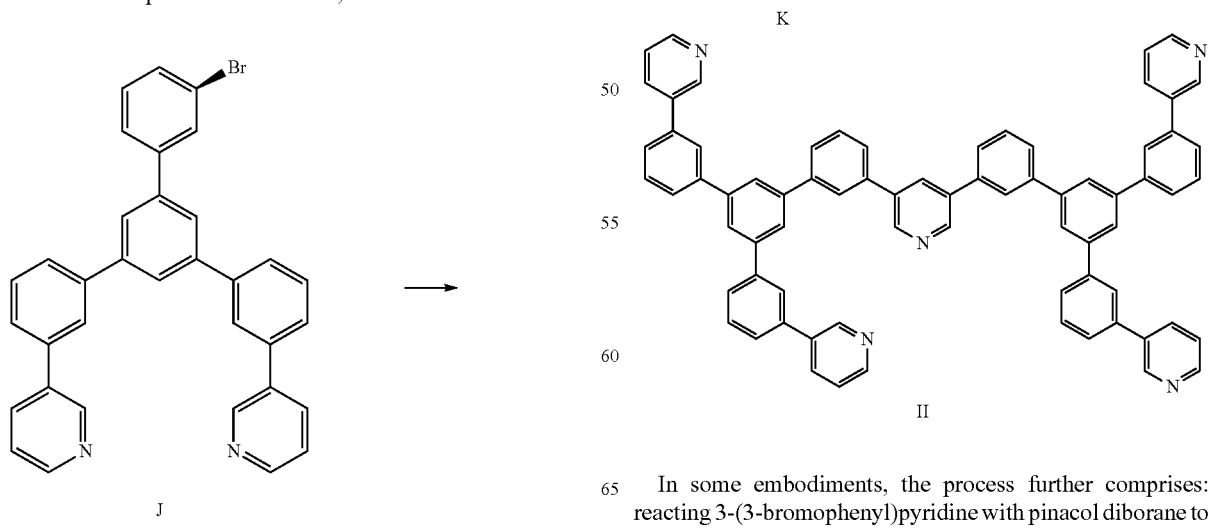

II

In some embodiments, the process further comprises: reacting 3-(3-bromophenyl)pyridine with pinacol diborane to form the compound of formula F.

In some embodiments, the process further comprises: reacting 1-bromo-3-iodobenzene with 3-pyridine boronic acid to form 3-(3-bromophenyl)pyridine.

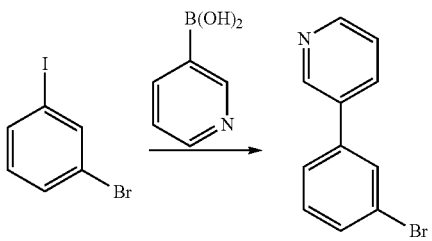 [SMILES: Brc1cccc(I)c1 ; OB(O)c1cccnc1 ; Brc1cccc(-c2cccnc2)c1]

The process described herein significantly increases yields of the intermediates, compounds of formula C and E by choosing selective reactivity of halides, trifluoromethanesulfonate, or hydroxy and in turn increases yields of the product, compounds of formula II and III. The process described herein can omit column chromatography for some steps and has higher yield, lower cost and higher productivity, and is thus suitable for mass production.

The process comprises Suzuki cross-coupling reactions in a suitable solvent, in the presence of a base and Pd catalyst. The reaction mixture is heated under an inert atmosphere for a period of time. Suitable solvents include but are not limited to dioxane, THF, EtOH, toluene and mixtures thereof. Exemplary bases include KOAc, $Na_2CO_3$, $K_2CO_3$, $Cs_2CO_3$, potassium phosphate and hydrates thereof. The bases can be added to the reaction as a solid powder or as an aqueous solution. The most commonly used catalysts include $Pd(PPh_3)_4$, $Pd_2(dba)_3$, or $Pd(OAc)_2$, $Pd(dba)_2$ with the addition of a secondary ligand. Exemplary ligands include dialkylphosphinobiphenyl ligands, such as structures V-IX shown below, in which Cy is cyclohexyl.

V

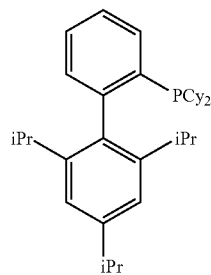

VI

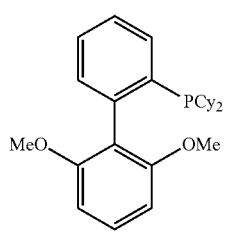

VII

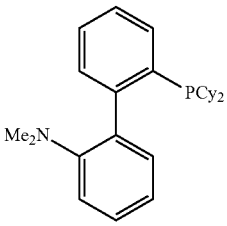

VIII

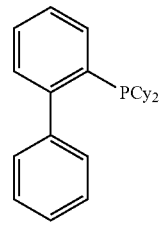

IX

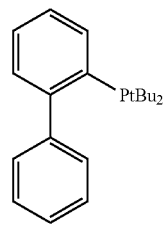

Compounds of formula I-IV have properties useful in optoelectronic devices, e.g., organic light emitting devices (OLEDs), and are particularly well suited for use as electron transporting materials and hole blocking materials for OLEDs as they have LUMO (Lowest Unoccupied Molecular Orbital) between 2.0 eV and 3.0 eV, and HOMO (Highest Occupied Molecular Orbital) typically greater than 5.5 eV, most greater than 6.0 eV.

An optoelectronic device, e.g., an OLED, typically includes in the simplest case, an anode layer and a corresponding cathode layer with an organic electroluminescent layer disposed between said anode and said cathode. When a voltage bias is applied across the electrodes, electrons are injected by the cathode into the electroluminescent layer while electrons are removed from (or "holes" are "injected" into) the electroluminescent layer from the anode. Light emission occurs as holes combine with electrons within the electroluminescent layer to form singlet or triplet excitons, light emission occurring as singlet and/or triplet excitons decay to their ground states via radiative decay.

Other components which may be present in an OLED in addition to the anode, cathode and light emitting material include a hole injection layer, an electron injection layer, and an electron transport layer. The electron transport layer need not be in direct contact with the cathode, and frequently the electron transport layer also serves as a hole blocking layer to prevent holes migrating toward the cathode. Additional components which may be present in an organic light-emitting device include hole transporting layers, hole transporting emission (emitting) layers and electron transporting emission (emitting) layers.

In one embodiment, the OLEDs comprising the organic compounds of the invention may be a fluorescent OLED comprising a singlet emitter. In another embodiment, the OLEDs comprising the organic compounds of the invention may be a phosphorescent OLED comprising at least one triplet emitter. In another embodiment, the OLEDs comprising the organic compounds of the invention comprise at least one singlet emitter and at least one triplet emitter. The OLEDs comprising the organic compounds of the invention may contain one or more, any or a combination of blue, yellow, orange, red phosphorescent dyes, including complexes of transition metals such as Ir, Os and Pt. In particular, electrophosphorescent and electrofluorescent metal complexes, such as those supplied by American Dye Source, Inc., Quebec, Canada may be used. Compounds of the formula I to IV may be part of an emissive layer, or hole transporting layer or electron transporting layer, or electron injection layer of an OLED or any combination thereof.

The organic electroluminescent layer, i.e., the emissive layer, is a layer within an organic light emitting device which when in operation contains a significant concentration of both electrons and holes and provides sites for exciton formation and light emission. A hole injection layer is a layer in contact with the anode which promotes the injection of holes from the anode into the interior layers of the OLED; and an electron injection layer is a layer in contact with the cathode that promotes the injection of electrons from the cathode into the OLED; an electron transport layer is a layer which facilitates conduction of electrons from the cathode and/or the electron injection layer to a charge recombination site. During operation of an organic light emitting device comprising an electron transport layer, the majority of charge carriers (i.e. holes and electrons) present in the electron transport layer are electrons and light emission can occur through recombination of holes and electrons present in the emissive layer. A hole transporting layer is a layer which when the OLED is in operation facilitates conduction of holes from the anode and/or the hole injection layer to charge recombination sites and which need not be in direct contact with the anode. A hole transporting emission layer is a layer in which when the OLED is in operation facilitates the conduction of holes to charge recombination sites, and in which the majority of charge carriers are holes, and in which emission occurs not only through recombination with residual electrons, but also through the transfer of energy from a charge recombination zone elsewhere in the device. An electron transporting emission layer is a layer in which when the OLED is in operation facilitates the conduction of electrons to charge recombination sites, and in which the majority of charge carriers are electrons, and in which emission occurs not only through recombination with residual holes, but also through the transfer of energy from a charge recombination zone elsewhere in the device.

Materials suitable for use as the anode includes materials having a bulk resistivity of preferred about 1000 ohms per square, as measured by a four-point probe technique. Indium tin oxide (ITO) is frequently used as the anode because it is substantially transparent to light transmission and thus facilitates the escape of light emitted from electro-active organic layer. Other materials, which may be utilized as the anode layer, include tin oxide, indium oxide, zinc oxide, indium zinc oxide, zinc indium tin oxide, antimony oxide, and mixtures thereof.

Materials suitable for use as the cathode include general electrical conductors including, but not limited to metals and metal oxides such as ITO etc which can inject negative charge carriers (electrons) into the inner layer(s) of the OLED. Various metals suitable for use as the cathode include K, Li, Na, Cs, Mg, Ca, Sr, Ba, Al, Ag, Au, In, Sn, Zn, Zr, Sc, Y, elements of the lanthanide series, alloys thereof, and mixtures thereof. Suitable alloy materials for use as the cathode layer include Ag—Mg, Al—Li, In—Mg, Al—Ca, and Al—Au alloys. Layered non-alloy structures may also be employed in the cathode, such as a thin layer of a metal such as calcium, or a metal fluoride, such as LiF, covered by a thicker layer of a metal, such as aluminum or silver. In particular, the cathode may be composed of a single metal, and especially of aluminum metal.

Compounds of formula I to IV may be used in electron transport layers in place of, or in addition to traditional materials such as poly(9,9-dioctyl fluorene), tris(8-hydroxyquinolato) aluminum ($Alq_3$), 2,9-dimethyl-4,7-diphenyl-1,1-phenanthroline, 4,7-diphenyl-1,10-phenanthroline, 2-(4-biphenylyl)-5-(4-t-butylphenyl)-1,3,4-oxadiazole, 3-(4-biphenylyl)-4-phenyl-5-(4-t-butylphenyl)-1,2,4-triazole, 1,3,4-oxadiazole-containing polymers, 1,3,4-triazole-containing polymers, quinoxaline-containing polymers, and cyano-PPV.

Materials suitable for use in hole transporting layers include 1,1-bis((di-4-tolylamino) phenyl)cyclohexane, N,N'-bis(4-methylphenyl)-N,N'-bis(4-ethylphenyl)-(1,1'-(3,3'-dimethyl)biphenyl)-4,4'-diamine, tetrakis-(3-methylphenyl)-N,N,N',N'-2,5-phenylenediamine, phenyl-4-N,N-diphenylaminostyrene, p-(diethylamino)benzaldehyde diphenylhydrazone, triphenylamine, 1-phenyl-3-(p-(diethylamino)styryl)-5-(p-(diethylamino)phenyl)pyrazoline, 1,2-trans-bis(9H-carbazol-9-yl)cyclobutane, N,N,N',N'-tetrakis (4-methylphenyl)-(1,1'-biphenyl)-4,4'-diamine, copper phthalocyanine, polyvinylcarbazole, (phenylmethyl)polysilane; poly(3,4-ethylendioxythiophene) (PEDOT), polyaniline, polyvinylcarbazole, triaryldiamine, tetraphenyldiamine, aromatic tertiary amines, hydrazone derivatives, carbazole derivatives, triazole derivatives, imidazole derivatives, oxadiazole derivatives having an amino group, and polythiophenes as disclosed in U.S. Pat. No. 6,023,371.

Materials suitable for use in the light emitting layer include electroluminescent polymers such as polyfluorenes, preferably poly(9,9-dioctyl fluorene) and copolymers thereof, such as poly(9,9'-dioctylfluorene-co-bis-N,N'-(4-butylphenyl) diphenylamine) (F8-TFB); poly(vinylcarbazole) and polyphenylenevinylene and their derivatives. In addition, the light emitting layer may include a blue, yellow, orange, green or red phosphorescent dye or metal complex, or a combination thereof. Materials suitable for use as the phosphorescent dye include, but are not limited to, tris(1-phenylisoquinoline) iridium (III) (red dye), tris(2-phenylpyridine) iridium (green dye) and Iridium (III) bis(2-(4,6-difluorephenyl)pyridinato-N,C2) (blue dye). Commercially available electrofluorescent and electrophosphorescent metal complexes from ADS (American Dyes Source, Inc.) may also be used. ADS green dyes include ADS060GE, ADS061GE, ADS063GE, and ADS066GE, ADS078GE, and ADS090GE. ADS blue dyes include ADS064BE, ADS065BE, and ADS070BE. ADS red dyes include ADS067RE, ADS068RE, ADS069RE, ADS075RE, ADS076RE, ADS067RE, and ADS077RE.

Organic compounds of formula I to IV may form part of the electron transport layer or electron injection layer or light emissive layer of optoelectronic devices, e.g., OLEDs. The OLEDs may be phosphorescent containing one or more, any or a combination of, blue, yellow, orange, green, red phosphorescent dyes.

Definitions

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical"

includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), and anthraceneyl groups (n=3). The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —$OPhC(CF_3)_2PhO$—), 4-chloromethylphen-1-yl, 3-trifluorovinyl-2-thienyl, 3-trichloromethylphen-1-yl (i.e., 3-$CCl_3Ph$-), 4-(3-bromoprop-1-yl)phen-1-yl (i.e., 4-$BrCH_2CH_2CH_2Ph$-), and the like. Further examples of aromatic radicals include 4-allyloxyphen-1-oxy, 4-aminophen-1-yl (i.e., 4-$H_2NPh$-), 3-aminocarbonylphen-1-yl (i.e., $NH_2COPh$-), 4-benzoylphen-1-yl, dicyanomethylidenebis(4-phen-1-yloxy) (i.e., —$OPhC(CN)_2PhO$—), 3-methylphen-1-yl, methylenebis(4-phen-1-yloxy) (i.e., —$OPhCH_2PhO$—), 2-ethylphen-1-yl, phenylethenyl, 3-formyl-2-thienyl, 2-hexyl-5-furanyl, hexamethylene-1,6-bis(4-phen-1-yloxy) (i.e., —$OPh(CH_2)_6PhO$—), 4-hydroxymethylphen-1-yl (i.e., 4-$HOCH_2Ph$-), 4-mercaptomethylphen-1-yl (i.e., 4-$HSCH_2Ph$-), 4-methylthiophen-1-yl (i.e., 4-$CH_3SPh$-), 3-methoxyphen-1-yl, 2-methoxycarbonylphen-1-yloxy (e.g. methyl salicyl), 2-nitromethylphen-1-yl (i.e., 2-$NO_2CH_2Ph$), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}C(CF_3)_2C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. $CH_3CHBrCH_2C_6H_{10}O$—), and the like. Further examples of cycloaliphatic radicals include 4-allyloxycyclohex-1-yl, 4-aminocyclohex-1-yl (i.e., $H_2NC_6H_{10}$—), 4-aminocarbonylcyclopent-1-yl (i.e., $NH_2COC_5H_8$—), 4-acetyloxycyclohex-1-yl, 2,2-dicyanoisopropylidenebis(cyclohex-4-yloxy) (i.e., —$OC_6H_{10}C(CN)_2C_6H_{10}O$—), 3-methylcyclohex-1-yl, methylenebis(cyclohex-4-yloxy) (i.e., —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —$OC_6H_{10}(CH_2)_6C_6H_{10}O$—), 4-hydroxymethylcyclohex-1-yl (i.e., 4-$HOCH_2C_6H_{10}$—), 4-mercaptomethylcyclohex-1-yl (i.e., 4-$HSCH_2C_6H_{10}$—), 4-methylthiocyclohex-1-yl (i.e., 4-$CH_3SC_6H_{10}$—), 4-methoxycyclohex-1-yl, 2-methoxycarbonylcyclohex-1-yloxy(2-$CH_3OCOC_6H_{10}O$—), 4-nitromethylcyclohex-1-yl (i.e., $NO_2CH_2C_6H_{10}$—), 3-trimethylsilylcyclohex-1-yl, 2-t-butyldimethylsilylcyclopent-1-yl, 4-trimethoxysilylethylcyclohex-1-yl (e.g. $(CH_3O)_3SiCH_2CH_2C_6H_{10}$—), 4-vinylcyclohexen-1-yl, vinylidenebis(cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" organic radicals substituted with a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g. —CH$_2$CHBrCH$_2$—), and the like. Further examples of aliphatic radicals include allyl, aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e. —CHO), hexyl, hexamethylene, hydroxymethyl (i.e. —CH$_2$OH), mercaptomethyl (i.e., —CH$_2$SH), methylthio (i.e., —SCH$_3$), methylthiomethyl (i.e.,—CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si—), t-butyldimethylsilyl, 3-trimethyoxysilypropyl (i.e., (CH$_3$O)$_3$SiCH$_2$CH$_2$CH$_2$—), vinyl, vinylidene, and the like. By way of further example, a C$_1$-C$_{10}$ aliphatic radical contains at least one but no more than 10 carbon atoms. A methyl group (i.e., CH$_3$—) is an example of a C$_1$ aliphatic radical. A decyl group (i.e., CH$_3$(CH$_2$)$_9$—) is an example of a C$_{10}$ aliphatic radical.

The term "heteroaryl" as used herein refers to aromatic or unsaturated rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as an ether, methylene or ethylene moiety. The common linking group may also be a carbonyl as in phenyl pyridyl ketone. Examples of heteroaryl rings include thiophene, pyridine, isoxazole, pyrazole, pyrrole, furan, imidazole, indole, thiazole, benzimidazole, quinoline, isoquinoline, quinoxaline, pyrimidine, pyrazine, tetrazole, triazole, benzo-fused analogues of these groups, benzopyranone, phenylpyridine, tolylpyridine, benzothienylpyridine, phenylisoquinoline, dibenzoquinozaline, fluorenylpyridine, ketopyrrole, 2-phenylbenzoxazole, 2 phenylbenzothiazole, thienylpyridine, benzothienylpyridine, 3 methoxy-2-phenylpyridine, phenylimine, pyridylnaphthalene, pyridylpyrrole, pyridylimidazole, and phenylindole.

The term "aryl" is used herein to refer to an aromatic substituent which may be a single aromatic ring or multiple aromatic rings which are fused together, linked covalently, or linked to a common group such as an ether, methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t -butyl, i-butyl (or 2-methylpropyl), etc. In particular embodiments, alkyls have between 1 and 200 carbon atoms, between 1 and 50 carbon atoms or between 1 and 20 carbon atoms.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

EXAMPLES

Examples 1-12 describe the syntheses of compounds of formula II-III, and intermediates used in making them. All reagents were purchased from Aldrich Chemical Co., Milwaukee, Wis., USA unless otherwise specified and were used without further purification. All compounds were characterized by $^1$H-NMR and found to correspond to the structures shown.

Example 1

Synthesis of 3-(3-bromophenyl)pyridine

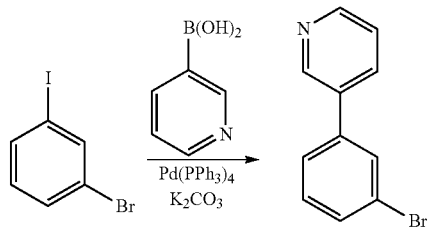 [SMILES: Brc1cccc(I)c1 ; OB(O)c1cccnc1 ; Brc1cccc(-c2cccnc2)c1]

1-bromo-3-iodobenzene (1.118 g, 3.95 mol) and 3-pyridine boronic acid (0.559 g, 4.54 mol) were added to a 100 mL three neck round bottom flask. To this flask, dioxane (20 mL) and aqueous K$_2$CO$_3$ (2 N, 20 mL) were added. The mixture was stirred and degassed with a steam of argon for 30 minutes. Then under argon atmosphere, 50 mg (0.04 mmol) of Pd(PPh$_3$)$_4$ (1%) was added. The mixture was heated to 100° C. and stirred overnight. The next day, the solvent was removed by roto-evaporation and the residue was suspended into an equal amount of water (50 mL) and CH$_2$Cl$_2$ (50 mL). The organic layer was separated from aqueous layer and washed with brine (50 mL×3). After drying over Na$_2$SO$_4$, and removal of the drying agent, about 0.92 g of 3-(3-bromophenyl)pyridine product (100%) was afforded. $^1$H NMR (400

MHz, CDCl$_3$) 8.85 (s, 1H), 8.65 (d, 1H), 7.87 (d, 1H), 7.75 (s, 1H), 7.57-7.52 (m, 2H), 7.41-7.35 (m, 2H).

Example 2

Synthesis of Compound of Formula F

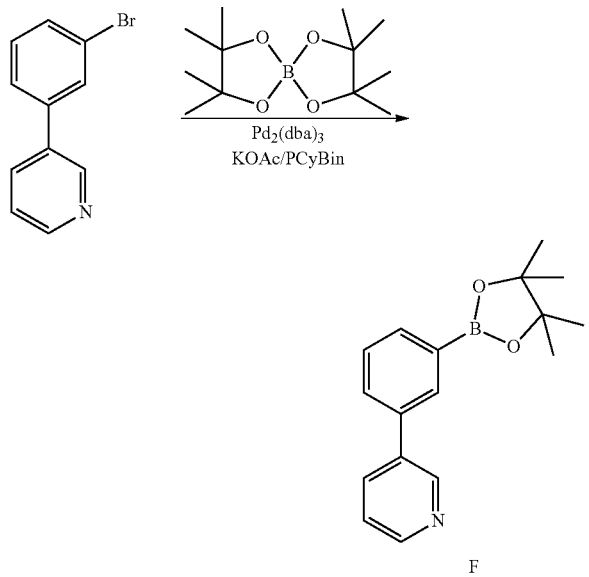

To a schlenk tube was charged 3-(3-bromophenyl)pyridine (4.18 g, 17.8 mmol), pinacol diborane (4.63 g, 18.2 mmol), dry KOAc (3.5 g, 35.7 mmol), ligand PCyBin (600 mg, 1.46 mmol, 8%) and Pd$_2$(dba)$_3$ (300 mg, 0.33 mmol, 2%). The Schlenk tube was evacuated and filled with argon three times. The Schlenk tube was placed in an argon atmosphere. Anhydrous dioxane (70 mL) was added. The Schlenk tube was then heated at 110° C. for 3 hours under argon atmosphere. An aliquot was removed (0.5 mL), filtered, washed with EtOAc, concentrated to dryness. This aliquot was analyzed by $^1$H NMR spectroscopy and revealed that all of the monobromide was converted into the corresponding boron ester. $^1$H NMR (400 MHz, CDCl$_3$) 8.90 (s, 1H), 8.60 (d, 1H), 8.05 (d, 1H), 7.95 (d, 1H), 7.87 (d, 1H), 7.70 (d, 1H), 7.53-7.49 (m, 1H), 7.40-7.37 (m, 1H), 1.38 (s, 12H).

Example 3

Synthesis of Compound of Formula G

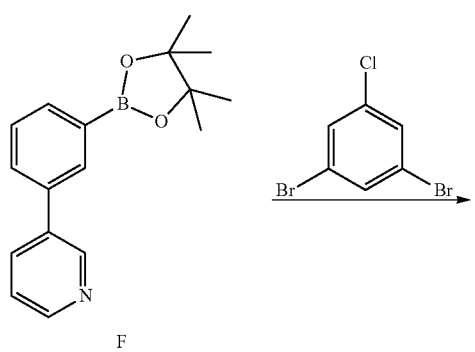

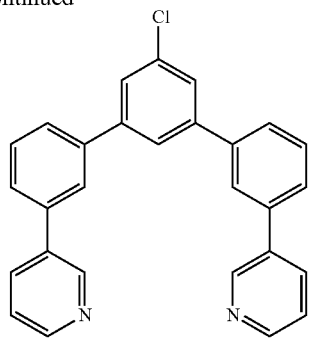

Potassium phosphate mono-hydrate (K$_3$PO$_4$.H$_2$O, 8 g, 40 mmol, 2 equiv) and 1-chloro-3,5-dibromobenzene (2.4 g, 8.93 mmol) were added into the reaction solution of EXAMPLE 2, then refluxed at 110° C. overnight under argon atmosphere. Then cooled to ambient temperature. Distilled water (30 mL) was added via a funnel, and the resulting mixture was filtered on a Büchner funnel. The filtrate was transferred to a separatory funnel and extracted with CH$_2$Cl$_2$ (3×50 mL). The combined organic phases were dried over Na$_2$SO$_4$, filtered on filter paper and concentrated to dryness by rotary evaporation (30° C., 25 mmHg). The resulting yellow solid was purified by column chromatography to afford 3.33 g white solid (90%). Compound G: $^1$H NMR (400 MHz, CDCl$_3$). 8.97 (s, 2H), 8.67 (d, 2H), 8.08 (d, 2H), 7.84 (s, 2H), 7.76 (s, 1H), 7.73-7.71 (m, 2H), 7.66-7.63 (m, 6H), 7.54-7.50 (m, 2H).

Example 4

Synthesis of Compound H

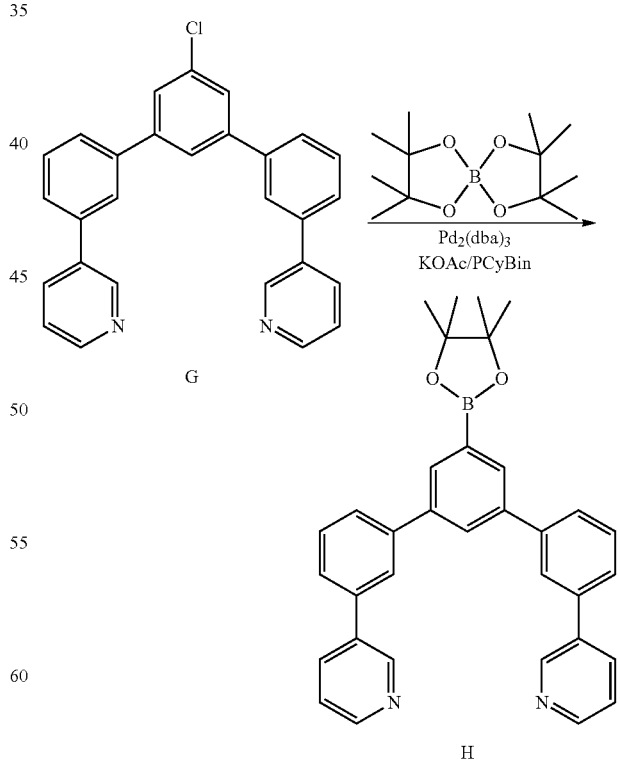

To a schlenk tube was charged compound G (1.57 g, 3.8 mmol), pinacol diborane (1.00 g, 3.9 mmol), dry KOAc (0.74 g, 7.6 mmol), ligand PCyBin (140 mg, 0.34 mmol, 8%) and Pd$_2$(dba)$_3$ (70 mg, 0.076 mmol, 2%). The Schlenk tube was evacuated and filled with argon three times. The Schlenk tube was placed in an argon atmosphere. Anhydrous dioxane (15 mL) was added. The Schlenk tube was then heated at 110° C. for 5 hours under argon atmosphere. An aliquot was removed (0.5 mL), filtered, washed with EtOAc, concentrated to dryness. This aliquot was analyzed by $^1$H NMR spectroscopy and revealed that all of the monobromide was converted into the corresponding boron ester. $^1$H NMR (400 MHz, CDCl$_3$) 8.98 (b, 2H), 8.67 (b, 2H), 8.12-8.08 (m, 4H), 7.99 (s, 1H), 7.89 (s, 2H), 7.80-7.76 (m, 2H), 7.62-7.60 (m, 4H), 7.55-7.51 (m, 2H), 1.41 (s, 12H).

Example 5

Synthesis of Compound of Formula J

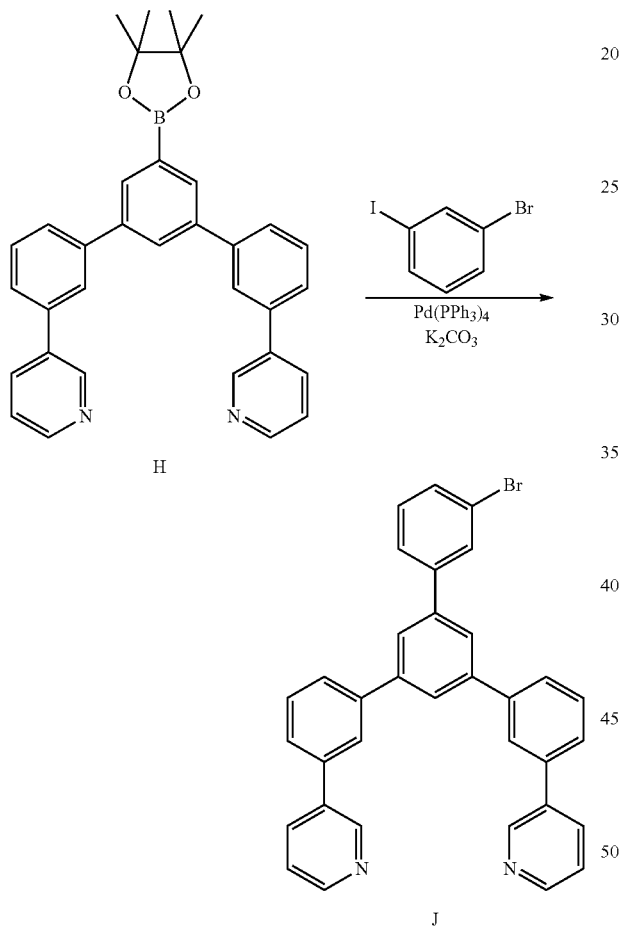

Compound H (0.71 g, 1.4 mmol), potassium carbonate (K$_2$CO$_3$, 2 N, 20 ml), Pd(PPh$_3$)$_4$ (50 g, 0.04 mol) and 1-bromo-3-iodobenzene (0.53 g, 1.87 mmol) were dissolved in 1,4-dioxane (20 ml), then refluxed at 110° C. overnight under argon atmosphere. Then cooled to ambient temperature. Distilled water (30 mL) was added via a funnel, and the resulting mixture was filtered on a Büchner funnel. The filtrate was transferred to a separatory funnel and extracted with CH$_2$Cl$_2$ (3×30 mL). The combined organic phases were dried over Na$_2$SO$_4$, filtered on filter paper and concentrated to dryness by rotary evaporation (30° C., 25 mmHg). The oil product was washed with hexane (2×20 mL), and precipitated in ethanol (20 mL) to yield yellow powder (~0.73 g, 97%) compound of formula J: $^1$H NMR (400 MHz, CDCl$_3$). 8.95 (s, 2H), 8.65 (d, 2H), 7.98 (d, 2H), 7.91-7.88 (m, 4H), 7.84 (s, 2H), 7.78-7.75 (m, 2H), 7.68-7.64 (m, 5H), 7.56 (d, 1H), 7.44-7.38 (m, 3H).

Example 6

Synthesis of Compound of Formula K

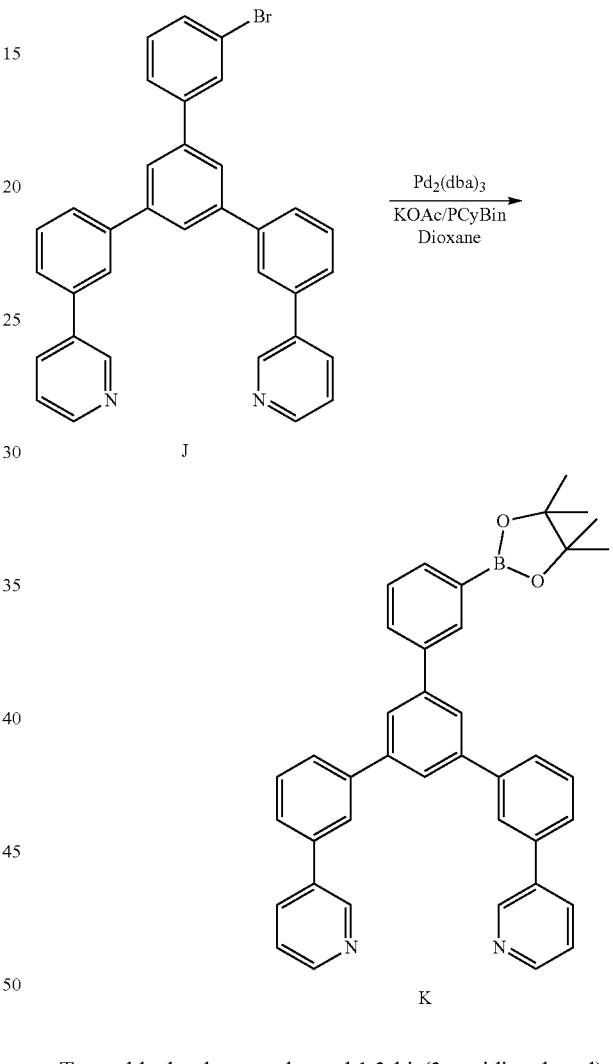

To a schlenk tube was charged 1,3-bis(3-pyridinephenyl)-5-(3-bromophenyl)benzene (compound J, 5.7 g, 10.55 mmol), pinacol diborane (2.82 g, 11.10 mmol), dry KOAc (2.2 g, 21.1 mmol), ligand PCyBin (400 mg, 0.97 mmol, 8%) and Pd$_2$(dba)$_3$ (200 mg, 0.218 mmol, 2%). The schlenk tube was evacuated and filled with argon three times. The schlenk tube was placed in an argon atmosphere. Anhydrous dioxane (40 mL) was added. The Schlenk tube was then heated at 110° C. for 5 hours under argon atmosphere. An aliquot was removed (0.5 mL), filtered, washed with EtOAc, concentrated to dryness. This aliquot was analyzed by $^1$H NMR spectroscopy and revealed that all of the monobromide was converted into the corresponding boron ester. $^1$H NMR (400 MHz, CDCl$_3$) 8.95 (s, 2H), 8.65 (d, 2H), 8.15 (s, 1H), 7.99 (d, 2H), 7.90-7.82 (m, 7H), 7.78-7.74 (m, 2H), 7.64-7.61 (m, 4H), 7.55-7.50 (m, 1H), 7.44-7.40 (m, 2H), 1.38 (s, 12H).

Example 7

Synthesis of Compound of Formula II

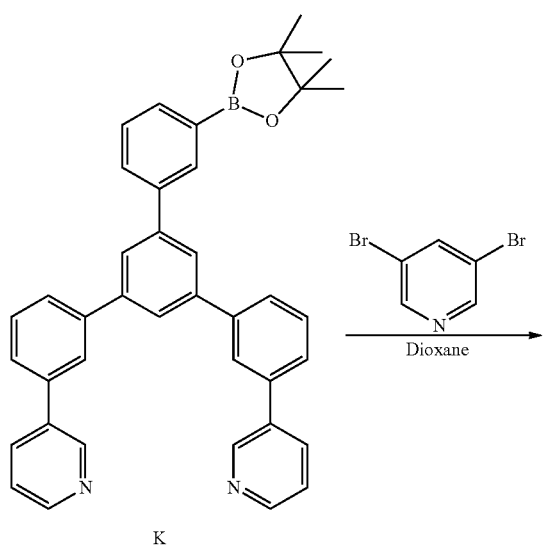

K

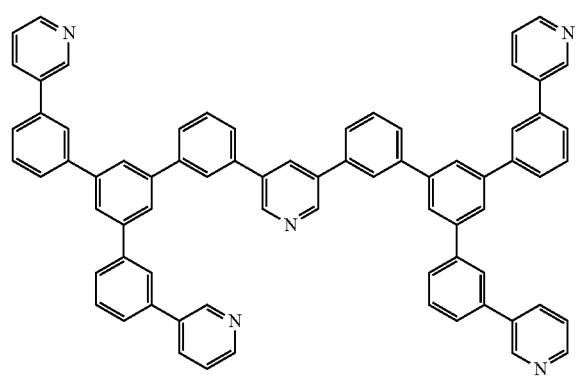

II

Potassium phosphate mono-hydrate ($K_3PO_4 \cdot H_2O$, 5 g, 25 mmol), 3,5-dibromopyridine (1080 mg, 4.58 mmol) and 5 ml DI water were added into the reaction solution of EXAMPLE 6, then refluxed at 110° C. overnight under argon atmosphere. Then cooled to ambient temperature. Distilled water (50 mL) was added via a funnel, and the resulting mixture was filtered on a Büchner funnel. The filtrate was transferred to a separatory funnel and extracted with $CH_2Cl_2$ (3×50 mL). The combined organic phases were dried over $Na_2SO_4$, filtered on filter paper and concentrated to dryness by rotary evaporation (30° C., 25 mmHg). The resulting yellow solid was purified by column chromatography to afford 4.0 g white solids (88%). $^1$H NMR (400 MHz, $CDCl_3$) δ 8.94 (m, 6H), 8.64 (m, 4H), 8.20 (m, 1H), 7.97-7.91 (m, 16H), 7.82-7.63 (m, 18H), 7.41 (m, 4H).

Example 8

Synthesis of Compound of Formula L

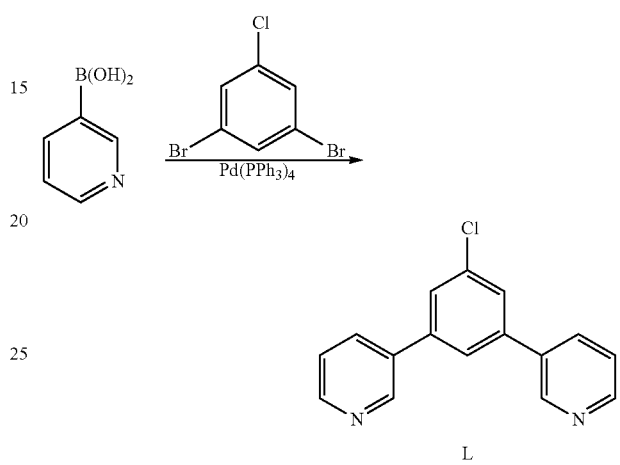

L 1-chloro-3,5-dibromobenzene (5.40 g, 20 mmol) and 3-pyridine boronic acid (5.17 g, 42 mmol) were added to a 100 mL three neck round bottom flask. To this flask, dioxane (80 mL) and aqueous $K_2CO_3$ (2 N, 40 mL) were added. The mixture was stirred and degassed with a steam of argon for 30 minutes. Then under argon atmosphere, 200 mg (0.16 mmol) $Pd(PPh_3)_4$ was added. The mixture was brought to 100° C. and stirred overnight. The next day, solvent was removed by roto-evaporation and residue was suspended into an equal amount of water (50 mL) and $CH_2Cl_2$ (50 mL). The organic layer was separated from aqueous layer and washed with brine (50 mL×3). After drying over $Na_2SO_4$, and removal of drying agent, ~5.33 g transparent liquid 3,3'-(5-chloro-1,3-phenylene)dipyridine (100%, Compound L) was obtained. $^1$H NMR (400 MHz, $CDCl_3$) 8.91 (s, 2H), 8.69 (d, 2H), 7.95 (d, 2H), 7.66 (s, 1H), 7.63 (s, 2H), 7.50-7.44 (m, 2H).

Example 9

Synthesis of Compound of Formula M

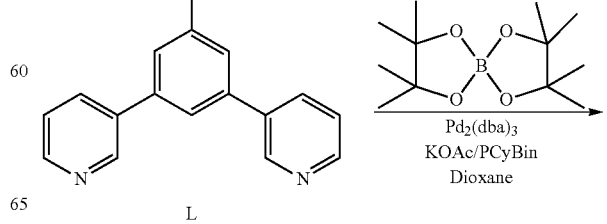

L

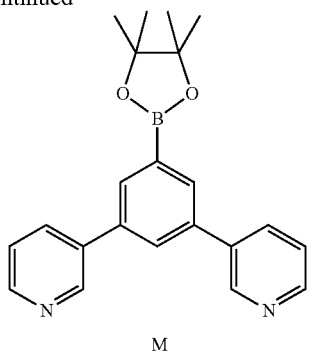

M

To a schlenk tube was charged compound L (5.35 g, 20 mmol), pinacol diborane (5.08 g, 20 mmol, 1.0 eq), dry KOAc (4.0 g, 40.8 mmol, 2 eq), ligand PCyBin (720 mg, 1.75 mmol, 8%) and Pd$_2$(dba)$_3$ (360 mg, 0.40 mmol, 2%). The Schlenk tube was evacuated and filled with argon three times. The Schlenk tube was placed in an argon atmosphere. Anhydrous dioxane (80 mL) was added. The Schlenk tube was then heated at 115° C. for 3 hours under argon atmosphere. An aliquot was removed (0.5 mL), filtered, washed with EtOAc, concentrated to dryness. This aliquot was analyzed by $^1$H NMR spectroscopy and revealed that all of the monobromide was converted into the corresponding boron ester. $^1$H NMR (400 MHz, CDCl$_3$) 8.94 (s, 2H), 8.64 (d, 2H), 8.08 (s, 2H), 8.00 (d, 2H), 7.86 (s, 1H), 7.45-7.39 (m, 2H), 1.39 (s, 12H).

Example 10

Synthesis of Compound of Formula N

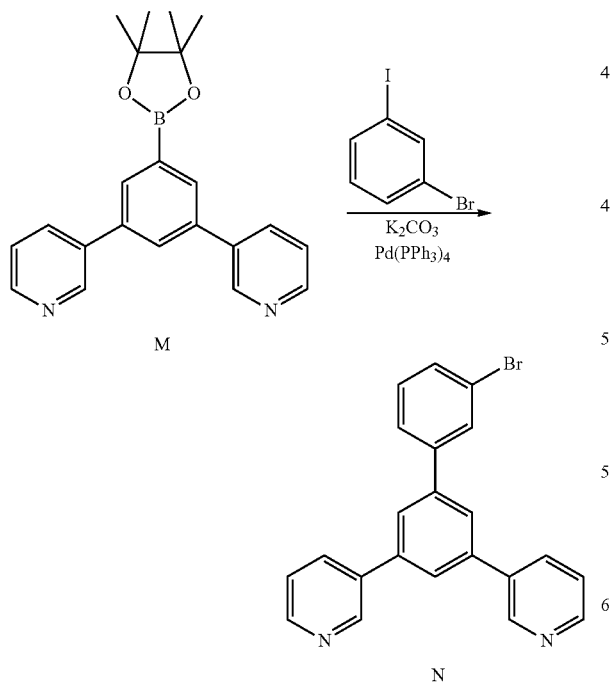

Compound M (3.58 g, 10 mmol) and 1-bromo-3-iodobenzene (3.68 g, 13 mmol) were added to a 100 mL three neck round bottom flask. To this flask, dioxane (40 mL) and aqueous K$_2$CO$_3$ (2 N, 40 mL) were added. The mixture was stirred and degassed with a steam of argon for 30 minutes. Then under argon atmosphere, 100 mg (0.08 mmol) Pd(PPh$_3$)$_4$ was added. The mixture was brought to 100° C. and stirred overnight. The next day, the solvent was removed by roto-evaporation and the residue was suspended into an equal amount of water (50 mL) and CH$_2$Cl$_2$ (50 mL). The organic layer was separated from the aqueous layer and washed with brine (50 mL×3). After drying over Na$_2$SO$_4$, and removal of drying agent, the oil product was washed with hexane (20 mL×3), and precipitated in methanol (20 mL) to yield white powder compound N (3.87 g, ~100%): $^1$H NMR (400 MHz, CDCl$_3$) 8.99 (s, 2H), 8.70 (s, 2H), 8.09 (d, 2H), 7.85 (s, 1H), 7.80 (d, 3H), 7.65-7.45 (m, 4H), 7.42-7.35 (m, 1H).

Example 11

Synthesis of Compound of Formula O

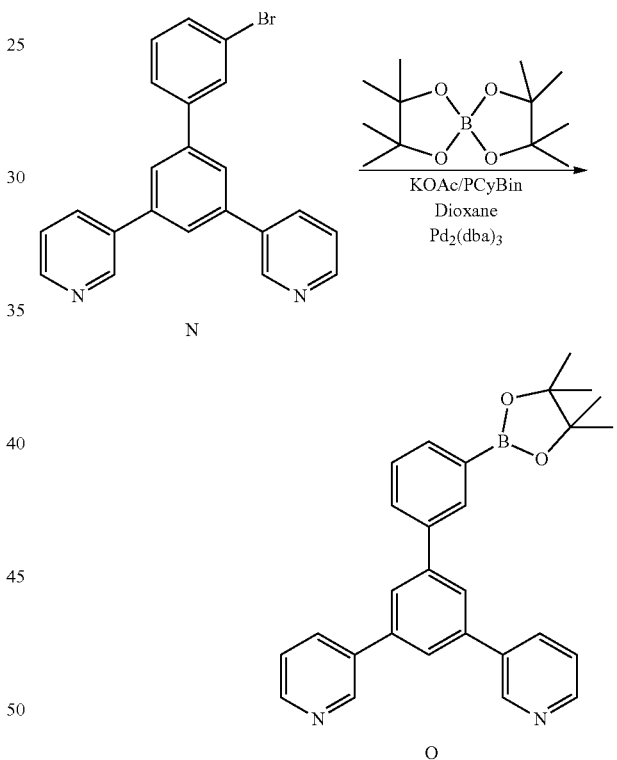

To a schlenk tube was charged 3,3'-(3'-bromobiphenyl-3,5-diyl)dipyridine (compound N, 2.0 g, 5.15 mmol), pinacol diborane (1.31 g, 5.15 mmol, 1.0 eq), dry KOAc (1.0 g, 10 mmol, 2 eq), ligand PCyBin (180 mg, 0.44 mmol, 8%) and Pd$_2$(dba)$_3$ (90 mg, 0.1 mmol, 2%). The schlenk tube was evacuated and filled with argon three times. The schlenk tube was placed in an argon atmosphere. Anhydrous dioxane (20 mL) was added. The Schlendk tube was then heated at 110° C. for 5 hours under argon atmosphere. An aliquot was removed (0.5 mL), filtered, washed with EtOAc, concentrated to dryness. This aliquot was analyzed by $^1$H NMR spectroscopy and revealed that all of the monobromide was converted into the corresponding boron ester. $^1$H NMR (400 MHz, CDCl$_3$) 8.95

(s, 2H), 8.65 (d, 2H), 8.11 (s, 1H), 8.03 (d, 2H), 7.88-7.85 (m, 3H), 7.78 (d, 1H), 7.73 (s, 1H), 7.53-7.43 (m, 3H), 1.37 (s, 12H).

Example 12

Synthesis of Compound of Formula III

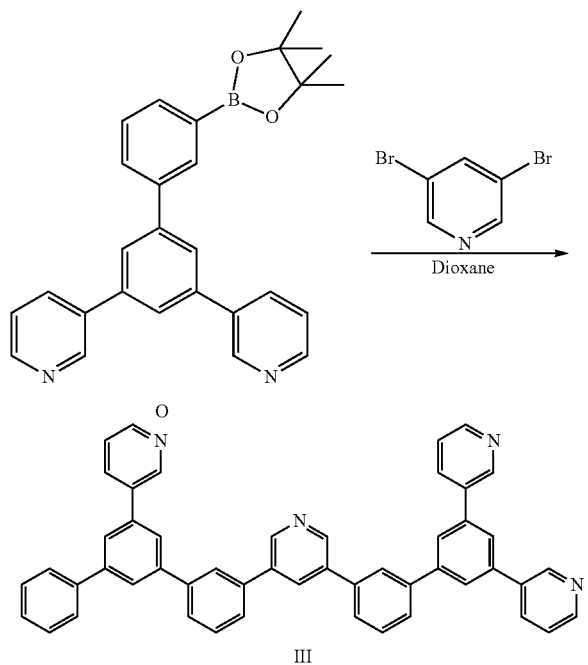

Potassium phosphate mono-hydrate ($K_3PO_4 \cdot H_2O$, 2.3 g, 10 mmol) and 3,5-dibromopyridine (567 mg, 2.4 mmol) were added into the reaction solution of EXAMPLE 11, then refluxed at 110° C. overnight under argon atmosphere. Then cooled to ambient temperature. Distilled water (50 mL) was added via a funnel, and the resulting mixture was filtered on a Büchner funnel. The filtrate was transferred to a separatory funnel and extracted with $CH_2Cl_2$ (3×30 mL). The combined organic phases were dried over $Na_2SO_4$, filtered on filter paper and concentrated to dryness by rotary evaporation (30° C., 25 mmHg). The resulting yellow solid was purified by column chromatography to afford 1.41 g (85%) white solid. $^1$H NMR (400 MHz, $CDCl_3$) 8.98 (s, 4H), 8.95 (s, 2H), 8.68 (d, 4H), 8.19 (s, 1H), 8.01 (d, 4H), 7.94 (s, 2H), 7.88 (s, 4H), 7.80-7.65 (m, 8H), 7.47-7.42 (m, 4H).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A compound of formula IV:

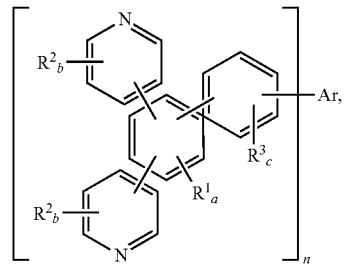

formula IV wherein
R$^1$, R$^2$, and R$^3$ are, independently at each occurrence, a $C_1$-$C_{20}$ aliphatic radical, a $C_3$-$C_{20}$ aromatic radical, or a $C_3$-$C_{20}$ cycloaliphatic radical;
Ar is

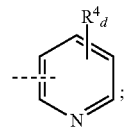

a is an integer ranging from 0-3;
b and c are, independently at each occurrence, an integer ranging from 0-4;
d is an integer ranging from 0-4;
R$^4$ is a $C_1$-$C_{20}$ aliphatic radical, a $C_3$-$C_{20}$ aromatic radical, or a $C_3$-$C_{20}$ cycloaliphatic radical and
n is an integer ranging from 2 to 4.
2. The compound of claim 1, wherein n is 2.
3. The compound of claim 2, wherein d is 0.
4. The compound of claim 2, wherein a is 0.
5. The compound of claim 2, wherein b is 0.
6. The compound of claim 2, wherein c is 0.
7. The compound of claim 2, being of formula III

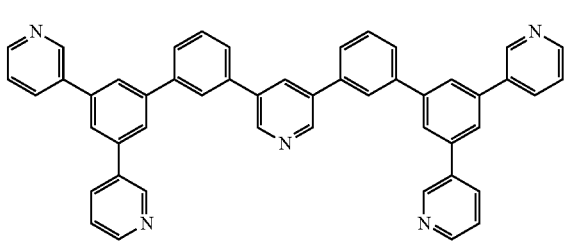

formula III

8. The compound of claim 1, wherein a is 0.
9. The compound of claim 1, wherein b is 0.
10. The compound of claim 1, wherein c is 0.
11. The compound of claim 1, wherein n is 2.

* * * * *